Oct. 11, 1966 J. McINTYRE Plant Pat. 2,680
HONEYLOCUST TREE
Filed Sept. 30, 1965
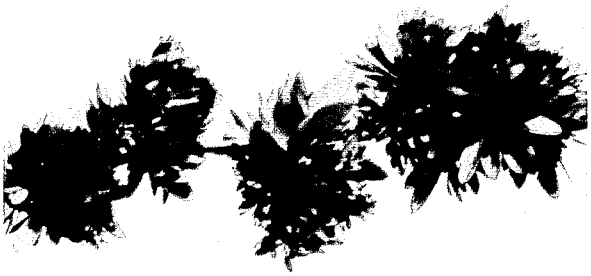
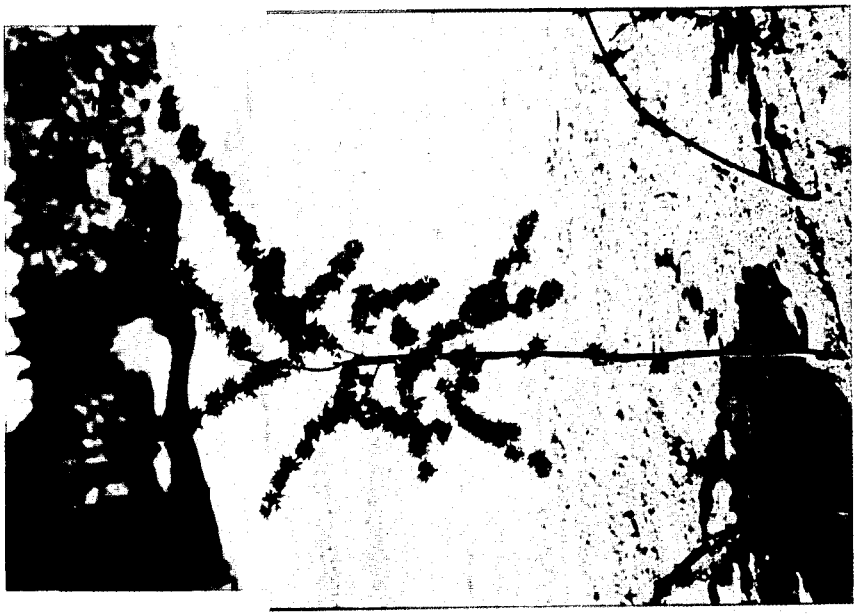
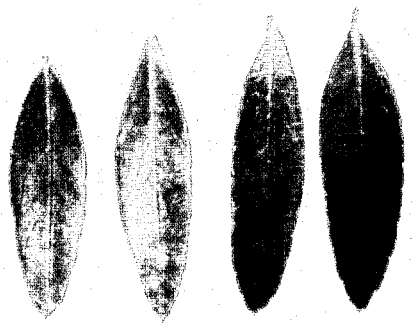
Inventor.
John Mc Intyre
By: Robb & Robb
Attorneys.

United States Patent Office

Plant Pat. 2,680
Patented Oct. 11, 1966

2,680
HONEYLOCUST TREE

John McIntyre, Gresham, Oreg., assignor to Wayne E. McGill, doing business as A. McGill & Son, Fairview, Oreg.

Filed Sept. 30, 1965, Ser. No. 491,852
1 Claim. (Cl. Plt.—52)

The present invention relates to a new and distinct variety of thornless and seedless honeylocust tree which was discovered by me on the cultivated nursery property of my assignee at Fairview, Oregon, as a newly found seedling of an unnamed and unpatented variety of *Gleditsia triacanthos inermis.*

Continued observations and tests of my new seedling, as well as progeny thereof derived from buddings made by me in the nursery aforementioned, have conclusively established that the seedling is definitely distinguished from its parent variety, as well as from all other varieties of which I am aware, as evidenced by the following unique combination of characteristics which are outstanding therein:

(1) A thornless and seedless habit;

(2) Compound leaves which are borne on very short leaf stems in the form of clusters along the branches; and (3) A green leaf color which is somewhat darker than that of the average thornless honeylocust.

The accompanying drawing shows a typical young tree specimen of my new seedling, as grown from budding in a nursery block of my assignee's nursery at Fairview, Oregon, as well as a typical specimen branch and typical individual leaf specimens on an enlarged scale and depicting both the upper and under surfaces of the leaves, all as illustrated in color as nearly true as it is reasonably possible to make the same in an illustration of this character.

The following is a detailed description of my new variety of honeylocust tree, with color terminology in accordance with the Exotica Horticultural Color Guide, published by Roehrs Company, of Rutherford, New Jersey:

Parentage: An unnamed seedling of *Gleditsia triacanthos inermis.*

Propagation: Holds its distinguishing characteristics through succeeding propagations by budding.

Locality where grown and observed: Fairview, Oregon.

Tree: Medium tall; open-spreading; hardy.

*Trunk.*—Moderately stout; smooth.

*Branches.*—Slender; smooth. Color—Green, Plate 83.

*Lenticels.*—Average for *Gleditsia triacanthos.*

Foliage:

*Leaves.*—Profuse quantity; compound of 80 to 100 leaves per cluster; medium thickness. Size: length—from 2 cm. to 3 cm.; width—from 1 cm. to 2 cm. Shape—compound leafed; pinnate. Color: Mature—Green, Plate 84; new growth—Green, Plate 82; autumn—Yellow, Plate 4. Margin—remotely crenate serrate. Petiole—short; from 0.5 cm. to 1.0 cm. Glands—none. Stipules—none.

Flower buds: None.

Seeds: None.

Thorns: None.

I claim:

A new and distinct variety of honeylocust tree, substantially as herein shown and described, characterized particularly as to novelty by the unique combination of a seedless and thornless habit, a habit of bearing compound leaves which are produced on very short leaf stems in the form of clusters along the branches, and a green leaf color which is somewhat darker than that of the average thornless honeylocust.

No references cited.

ABRAHAM G. STONE, *Primary Examiner.*

R. E. BAGWILL, *Assistant Examiner.*